US011103571B2

(12) United States Patent
Lam et al.

(10) Patent No.: US 11,103,571 B2
(45) Date of Patent: Aug. 31, 2021

(54) EDIBLE VACCINES EXPRESSED IN YEAST FOR PREVENTING AND TREATING INFECTIOUS DISEASES IN ANIMALS AND HUMAN

(71) Applicants: Olivia Yee-Yee Lam, Los Angeles, CA (US); Dominic Man-Kit Lam, Hong Kong (CN); Han Lei, Hong Kong (CN); Fong Wilson Lam, Houston, TX (US)

(72) Inventors: Olivia Yee-Yee Lam, Los Angeles, CA (US); Dominic Man-Kit Lam, Hong Kong (CN); Han Lei, Hong Kong (CN); Fong Wilson Lam, Houston, TX (US)

( * ) Notice: Subject to any disclaimer, the term of this patent is extended or adjusted under 35 U.S.C. 154(b) by 0 days.

(21) Appl. No.: 16/847,342

(22) Filed: Apr. 13, 2020

(65) Prior Publication Data

US 2020/0353066 A1 Nov. 12, 2020

Related U.S. Application Data

(62) Division of application No. 15/648,863, filed on Jul. 13, 2017, now Pat. No. 10,617,751.

(51) Int. Cl.

| | |
|---|---|
| ***A01N 63/00*** | (2020.01) |
| ***A01H 3/00*** | (2006.01) |
| ***C07H 21/04*** | (2006.01) |
| ***C12N 15/67*** | (2006.01) |
| ***C12N 15/113*** | (2010.01) |
| ***A61K 39/12*** | (2006.01) |
| *A61K 39/00* | (2006.01) |

(52) U.S. Cl.

CPC ........ *A61K 39/12* (2013.01); *A61K 2039/522* (2013.01); *A61K 2039/523* (2013.01); *A61K 2039/54* (2013.01); *A61K 2039/552* (2013.01); *C12N 2710/18034* (2013.01)

(58) Field of Classification Search

CPC .......... A01H 3/00; A01N 63/00; A01N 63/10; C12N 15/67; C12N 15/72

See application file for complete search history.

(56) References Cited

U.S. PATENT DOCUMENTS

| | | | |
|---|---|---|---|
| 5,484,719 | A | 1/1996 | Lam et al. |
| 5,612,487 | A | 3/1997 | Lam et al. |
| 5,654,184 | A | 8/1997 | Curtiss, III et al. |
| 5,670,349 | A | 9/1997 | Cramer et al. |
| 5,679,880 | A | 10/1997 | Curtiss, III et al. |
| 5,686,079 | A | 11/1997 | Curtiss, III et al. |
| 5,914,123 | A | 6/1999 | Arntzen et al. |
| 5,958,422 | A | 9/1999 | Lomonossoff |
| 6,034,298 | A | 3/2000 | Lam et al. |
| 6,136,320 | A | 10/2000 | Arntzen et al. |
| 7,504,560 | B2 | 3/2009 | Arntzen et al. |
| 10,617,751 | B2 | 4/2020 | Lam et al. |
| 2001/0053367 | A1 | 12/2001 | Arntzen et al. |
| 2012/0171230 | A1 | 7/2012 | Lam et al. |
| 2012/0276167 | A1 | 11/2012 | Lam et al. |

OTHER PUBLICATIONS

Wang, "A New Yeast Display Vector Permitting Free scFv AmMino Termini Can Augment Ligand Binding Affinities," Protein Engineering, Design & Selection, vol. 18, No. 7, 2005, pp. 337-343.

*Primary Examiner* — Barry A Chestnut

(57) ABSTRACT

In the invention described here, the approach is to formulate an edible vaccine based on N-terminal yeast surface display expression systems including *S. cerevisiae* EBY100/pYD5-VP28, *S. cerevisiae* EBY100/pYD5-VP28-VP24 and *S. cerevisiae* EBY100/pYD5-VP24 for preventing shrimps such as *L. vannamei, P. monodon* and *M. rosenbergii* species from white spot syndrome virus (WSSV) infection, suggesting that yeast surface display expression system expressing WSSV antigen has potential as a prophylactic treatment for WSSV in shrimps via oral vaccination. The technology developed in this patent application can also be used to produce edible (oral) vaccines for preventing and treating other infectious diseases in animals and human.

6 Claims, No Drawings

Specification includes a Sequence Listing.

EDIBLE VACCINES EXPRESSED IN YEAST FOR PREVENTING AND TREATING INFECTIOUS DISEASES IN ANIMALS AND HUMAN

CROSS-REFERENCE TO RELATED APPLICATION

This application is a divisional application of U.S. application Ser. No. 15/648,863, filed Jul. 13, 2017 (now U.S. Pat. No. 10,617,751; issued Apr. 14, 2020), which application is hereby incorporated in its entirety by reference for all purposes.

SEQUENCE LISTING

The instant application contains a Sequence listing which has been submitted electronically in ASCII format via EFS-Web and is hereby incorporated by reference in its entirety. Said ASCII copy, created on Jun. 18, 2020, is named MSQ-001D1_SL.txt and is 4 kilobytes in size.

FIELD OF THE INVENTION

The present invention is for the composition of an edible vaccine based on yeast surface display expressions for creating an edible vaccine that prevents and treats infections in animals and humans, including, but not limited to, preventing shrimps from being infected with white spot syndrome (WSSV). The present invention comprises mainly a N-terminal yeast surface expression system and oral vaccination in shrimps.

BACKGROUND OF THE INVENTION

White Spot Syndrome Virus (WSSV) is an infectious pathogen of shrimp and other crustaceans. Currently, there are no effective vaccines and adequate treatments available against WSSV. More importantly, conventional immune route such as injection is not suitable for shrimp vaccination. Therefore, oral administration is good way to deliver WSSV vaccine.

The concept of edible vaccines was proposed by Prof. Dominic Lam and executed by him and his colleagues in early 1990s who first reported the expression of hepatitis B virus surface antigen (HBsAg) in tomato. Edible vaccines will be more acceptable because of its oral rather than injectable route of application. In contrast, producing the vaccines in plants could reduce the cost to less than a penny per dose, and simple fast food processing like drying and grinding could create non-perishable preparations without refrigeration. Further, Prof. Dominic Lam and his research team also focus on *Lactococcus* based vaccines which are used to prevent avian influenza infection.

Yeast surface display technology has been extensively developed for application in preventing virus affection. Recently, *Saccharomyces cerevisiae* (*S. cerevisiae*) surface display was used to develop H5N1 vaccine. *P. pastoris* cell surface display system was used to express VP28 and Rab7, respectively. Unfortunately, there no further animal test for this system. Importantly, there are no attempts to develop WSSV vaccine using *S. cerevisiae* display system which is more efficient than *P. pastoris* for viral antigen display.

Invertebrates lack true adaptive immunity and it solely depends on the primitive immunity called innate immunity. However, various innate immune molecules and mechanisms are identified in shrimp that plays potential role against invading bacterial, fungal and viral pathogens. Perceiving the shrimp innate immune mechanisms will contribute in developing effective vaccine strategies against major shrimp pathogens.

Collectively, we propose this invention that *S. cerevisiae* surface display system can be used to develop WSSV vaccine. To address this invention, VP28 and VP24 antigen genes are investigated by *S. cerevisiae* N-terminal surface display platforms.

Although the mechanism underlying the interaction between WSSV and host cells remain unknown, VP28 (27.5 kDa) and VP24 (22 kDa) are generally considered major capsid antigen proteins of WSSV, which are involved in the infection process as an attachment protein. This is the primary reason why VP28 and VP24 of the white spot syndrome virus (WSSV) have been used as candidate antigens for potential vaccines development.

Vaccination is currently the only method that can effectively stop the spread of WSSV in shrimps. Conventional platform for WSSV vaccine shows poor immunity. In the present invention, we describe a new type of potent WSSV vaccine based on yeast surface display system.

The present invention can provide an effective way to protect shrimps from WSSV infection and may also be used to produce edible vaccines for preventing and treating other infectious diseases in animals and humans.

SUMMARY OF THE INVENTION

The present invention is about an edible vaccine for preventing WSSV infection in shrimps. The present invention describes that a N-terminal display plasmid, pYD5, to display VP28, VP24 or VP28-VP24 fusion protein on the surface of *S. cerevisiae* EBY100 and detected by Western blotting, immunofluorescence and flow cytometric assay. The recombinant yeast is mixed with pellets for feeding shrimps such as *L. vannamei, P. monodon* and *M. rosenbergii* species, followed by WSSV virus challenge. The present invention suggests that yeast display expression system can be developed for shrimp vaccines for preventing WSSV infection.

The present invention contains 3 major parts: (i) the construction of recombinant yeast. (ii) the recombinant yeast is mixed with feeding pellet. (iii) the vaccinated shrimps is challenged with WSSV.

DETAILED DESCRIPTION OF INVENTION

Construction of WSSV Antigen Surface-Displayed Yeast Vaccines

The VP28 gene (Gene accession No. KR057961.1) will be PCR-amplified using specific primers and subcloned into pYD5 in-frame with the endogenous Aga2p signal peptide sequence. The resultant shuttle plasmid pYD5-VP28 will be transformed into *E. coli* DH5a. The plasmid pYD5-VP28 will then be extracted from *E. coli*, purified and electroporated into competent *S. cerevisiae* EBY100 after being linearized. Recombinant yeast transformants will be plated on selective minimal dextrose plates containing amino acids (0.67% yeast nitrogen base without amino acids (YNB), 2% glucose, 0.01% leucine, 2% agar, and 1M sorbitol). $Trp^+$ transformants will be selected after 3 days of growth on the selective minimal dextrose plates.

The positive colonies are confirmed by genomic PCR. Recombinant *S. cerevisiae* EBY100/pYD5-VP28 is cultured in YNB-CAA-Glu (0.67% YNB, 0.5 casamino acids, 2% Glucose) and induced in YNB-CAA-Gal (0.67% YNB, 0.5 casamino acids, 2% Galactose, 13.61 g/L $Na_2HPO_4$, 7.48 g/L $NaH_2PO_4$ and 5 g/L casamino acids) at 20° C. with shaking (250 rpm) for inducing VP28 surface display. *S. cerevisiae* EBY 100 carrying pYD5 plasmid served as a negative control for all the tests.

Two additional types of vaccines will be constructed in this section:

*S. cerevisiae* EBY100/pYD5-VP24-VP24 surface displayed yeast vaccine.

*S. cerevisiae* EBY100/pYD5-VP28-VP24-VP28 and VP24 cosurface-displayed yeast vaccine.

Determining the Functional Display of WSSV Antigen on Yeast Surface

This experiment is designed to validate the functional display of the WSSV antigen on yeast surface.

Western Blotting

1 $OD_{600}$ (1 $OD_{600} \approx 10^7$ cells) equivalent recombinant yeast will be collected at different time point post inducement with 2% galactose. The samples are washed three times with 500 μl of PBS, re-suspended in 50 μl of 6×SDS loading buffer (Bio-Rad, Hercules, Calif.), and boiled for 10 min. The surface presented VP28 will be extracted by heating 1 $OD_{600}$ of *S. cerevisiae* EBY100/pYD5-VP28 pellets at 95° C. in a Bromophenol blue sample buffer supplemented with 5%-ME for 5 min. The samples were then resolved on a 4-15% SDS-PAGE gel (Bio-Rad), and transferred to 0.45 □m nitrocellulose membranes (Bio-Rad). After blocking with 5% non-fat milk at room temperature for 2 h, the membrane will be incubated with polyclonal rabbit anti-VP28 antibody (Thermo) as primary antibody (1:500 diluted). After incubated overnight at 4° C. and washed three times using PBS buffer, the membranes will be reacted to the secondary antibodies, horseradish peroxidase (HRP)-conjugated goat anti-rabbit IgG (1:5,000 diluted) (Sigma-Aldrich Co., St. Louis, Mo.) for 1 hour at room temperature. The signal will be generated using West Pico chemiluminescent substrates (Thermo Fisher Scientific Inc., Rockford, Ill.) and detected using a ChemiDoc XRS System (Bio-Rad).

Glycosylation Analysis of Yeast Surface Displayed VP28

PNGase F is obtained from New England Labs (Beverly, Mass.). Recombinant *S. cerevisiae* EBY100/pYD5-VP28 will be cultured at 30° C. in YNB-CAA-Glu overnight and then induced at 20° C. in YNB-CAA-Gal for 72 hours. 1 $OD_{600}$ equivalent cells will be collected, centrifuged, and washed once in a PBS buffer. Cell pellets were denatured at 100° C. for 10 min in a denaturing buffer included in the PNGase F reagent. A portion of 1 μL of PNGase F (5,000 U) will be added to the denatured protein solution, followed by incubation at 37° C. for 1 hour according to the manufacturer's instruction. The treated samples will then be subjected to Western blotting analysis.

Immunofluorescence Microscopy

To detect VP28 display on yeast surface, recombinant *S. cerevisiae* EBY100/pYD5-VP28 will be collected in a 24-hour interval over a 72-hour time period after inducement with galactose (2%). 1 $OD_{600}$ equivalent recombinant yeast will be collected and blocked with 5% non-fat milk in PBS for 1 hour, and incubated with polyclonal rabbit anti-VP28 antibodies (1:500 diluted) at 4° C. for 1 hour. After washing with PBS, the samples will be incubated with goat anti-rabbit IgG FITC conjugates (Sigma) (1:5,000 diluted) at room temperature for 1 h. The samples will be kept in dark until use. The FITC labeled yeast will be examined under an inverted phase contrast fluorescence microscope.

Flow Cytometric Assay

After inducement with galactose (2%), 1 $OD_{600}$ equivalent recombinant yeasts will be collected over a 72-hour time period, with a 24-hour interval, as described above. The cell samples will be washed three times with sterile PBS containing 1% bovine serum albumin (BSA) and incubated with polyclonal rabbit anti-VP28 antibodies from BEI Resources (NR-2729) (1:500 diluted) at 4° C. for 1 hour, followed by reacting with FITC-conjugated goat anti-rabbit IgG (1:5,000) at 4° C. for 30 min. The cell samples will be re-suspended in 500 μL of sterile PBS and will be subject to flow cytometric analysis using a BD FACS Aira III (BD Bioscience, San Jose, Calif.). *S. cerevisiae* EBY100/pYD5 served as a negative control for the assay. These data will be used to ascertain which time point will be the best for collecting yeast vaccines that present the highest level of VP28 on their surface.

Note: The similar methods are used to determine the functional display for the following yeast vaccines (*S. cerevisiae* EBY100/pYD5-VP28-VP24 and *S. cerevisiae* EBY100/pYD5-VP24).

Optimization of Oral Immunization

Commercial shrimp pellet feed weighing 2 g were coated with 3 ml of $1 \times 10^8$ pfu/ml of recombinant yeast. The feed was mixed and incubated on ice for 30 min followed by room temperature (RT) incubation for 30 min to allow absorption. The pellets were coated with fish oil to prevent dispersion.

A batch of shrimp was divided into five groups and 20 shrimps per group were selected. The shrimp in group first, second and third were administrated orally with recombinant yeast-VP28, yeast-VP24 and yeast-VP28-VP24 coated feed continuously for 7 days, whereas group fourth and fifth were administrated orally with PBS and yeast containing empty plasmid coated feed, respectively.

Virus Challenge

Third day after final vaccination, the shrimp in group one to three were immersed in a sea water containing a dilution of 1:150 WSSV stock solution for 2 hrs, then the shrimp was changed in to fresh seawater without WSSV. Another batch of shrimp (5 groups, 20 shrimp each group), the vaccine experiment was repeated and shrimp were challenged with WSSV on 15 days post vaccination (dpv). The oral vaccination experiments were repeated three times.

Based on these results, we can evaluate and determine the strength and degree of immune protection that can be provided by the yeast vaccines. Further, we can determine which vaccine provides the complete immune protection of shrimps from virus challenge.

```
VP28 gene sequence (615 bp):
ATGGATCTTTCTTTCACTCTTTCGGTCGTGTCGGCCATCCTCGCCATCAC

TGCTGTGATTGCTGTATTTATTGTGATTTTTAGGTATCACAACACTGTGA

CCAAGACCATCGAAACCCACACAGACAATATCGAGACAAACATGGATGAA

AACCTCCGCATTCCTGTGACTGCTGAGGTTGGATCAGGCTACTTCAAGAT

GACTGATGTGTCCTTTGACAGCGACACCTTGGGCAAAATCAAGATCCGCA

ATGGAAAGTCTGATGCACAGATGAAGGAAGAAGATGCGGATCTTGTCATC

ACTCCCGTGGAGGGCCGAGCACTCGAAGTGACTGTGGGGCAGAATCTCAC

CTTTGAGGGAACATTCAAGGTGTGGAACAACACATCAAGAAAGATCAACA

TCACTGGTATGCAGATGGTGCCAAAGATTAACCCATCAAAGGCCTTTGTC

GGTAGCTCCAACACCTCCTCCTTCACCCCCGTCTCTATTGATGAGGATGA
```

-continued

AGTTGGCACCTTTGTGTGTGGTACCACCTTTGGCGCACCAATTGCAGCTA

CCGCCGGTGGAAATCTTTTCGACATGTACGTGCACGTCACCTACTCTGGC

ACTGAGACCGAGTAA

VP24 gene sequence (627 bp):
ATGCACATGTGGGGGGTTTACGCCGCTATACTGGCGGGTTTGACATTGAT

ACTCGTGGTTATATCTATAGTTGTAACCAACATAGAACTTAACAAGAAAT

TGGACAAGAAGGATAAAGACGCCTACCCTGTTGAATCTGAAATAATAAAC

TTGACCATTAACGGTGTTGCTAGAGGAAACCACTTTAACTTTGTAAACGG

CACATTACAAACCAGGAACTATGGAAAGGTATATGTAGCTGGCCAAGGAA

CGTCCGATTCTGAACTGGTAAAAAAGAAAGGAGACATAATCCTCACATCT

TTACTTGGAGACGGAGACCACACACTAAATGTAAACAAAGCCGAATCTAA

AGAATTAGAATTGTATGCAAGAGTATACAATAATACAAAGAGGGATATAA

CAGTGGACTCTGTTTCACTGTCTCCAGGTCTAAATGCTACAGGAAGGGAA

TTTTCAGCTAACAAATTTGTATTATATTTCAAACCAACAGTTTTGAAGAA

AAATAGGATCAACACACTTGTGTTTGGAGCAACGTTTGACGAAGACATCG

ATGATACAAATAGGCATTATCTGTTAAGTATGCGATTTTCTCCTGGCAAT

GATCTGTTTAAGGTTGGGGAAAAAATAA

VP28-VP24 gene sequence (1302 bp)
GCTAGCGTTTTAGCAGCTGGTGATCTTTCTTTCACTCTTTCGGTCGTGTC

GGCCATCCTCGCCATCACTGCTGTGATTGCTGTATTTATTGTGATTTTTA

GGTATCACAACACTGTGACCAAGACCATCGAAACCCACACAGACAATATC

GAGACAAACATGGATGAAAACCTCCGCATTCCTGTGACTGCTGAGGTTGG

ATCAGGCTACTTCAAGATGACTGATGTGTCCTTTGACAGCGACACCTTGG

-continued

GCAAAATCAAGATCCGCAATGGAAAGTCTGATGCACAGATGAAGGAAGAA

GATGCGGATCTTGTCATCACTCCCGTGGAGGGCCGAGCACTCGAAGTGAC

TGTGGGGCAGAATCTCACCTTTGAGGGAACATTCAAGGTGTGGAACAACA

CATCAAGAAAGATCAACATCACTGGTATGCAGATGGTGCCAAAGATTAAC

CCATCAAAGGCCTTTGTCGGTAGCTCCAACACCTCCTCCTTCACCCCCGT

CTCTATTGATGAGGATGAAGTTGGCACCTTTGTGTGTGGTACCACCTTTG

GCGCACCAATTGCAGCTACCGCCGGTGGAAATCTTTTCGACATGTACGTG

CACGTCACCTACTCTGGCACTGAGACCGAGGGTGGTGGTGGTTCTGGTGG

TGGTGGTTCTGGTGGTGGTGGTTCTCACATGTGGGGGGTTTACGCCGCTA

TACTGGCGGGTTTGACATTGATACTCGTGGTTATATCTATAGTTGTAACC

AACATAGAACTTAACAAGAAATTGGACAAGAAGGATAAAGACGCCTACCC

TGTTGAATCTGAAATAATAAACTTGACCATTAACGGTGTTGCTAGAGGAA

ACCACTTTAACTTTGTAAACGGCACATTACAAACCAGGAACTATGGAAAG

GTATATGTAGCTGGCCAAGGAACGTCCGATTCTGAACTGGTAAAAAAGAA

AGGAGACATAATCCTCACATCTTTACTTGGAGACGGAGACCACACACTAA

ATGTAAACAAAGCCGAATCTAAAGAATTAGAATTGTATGCAAGAGTATAC

AATAATACAAAGAGGGATATAACAGTGGACTCTGTTTCACTGTCTCCAGG

TCTAAATGCTACAGGAAGGGAATTTTCAGCTAACAAATTTGTATTATATT

TCAAACCAACAGTTTTGAAGAAAAATAGGATCAACACACTTGTGTTTGGA

GCAACGTTTGACGAAGACATCGATGATACAAATAGGCATTATCTGTTAAG

TATGCGATTTTCTCCTGGCAATGATCTGTTTAAGGTTGGGGAAAAAGAAT

TC

---

What is claimed is:

1. A method of immunizing shrimp against white spot syndrome virus (WSSV) comprising the step of administering to the shrimp a shrimp pellet feed coated with a recombinant yeast cell, wherein said recombinant yeast cell expresses, on its surface, a white spot syndrome virus (WSSV) antigen selected from the group consisting of VP24, VP28, and a combination of VP24 and VP28.

2. The method of claim 1, wherein administering comprises administering continuously for 7 days.

3. A method of making a vaccine against white spot syndrome virus (WSSV) comprising a step of:

a) coating shrimp pellet feed with a recombinant yeast cell, wherein said recombinant yeast cell expresses, on its surface, a white spot syndrome virus (WSSV) antigen selected from the group consisting of VP24, VP28, and a combination of VP24 and VP28; and b) incubating the shrimp pellet feed.

4. The method of claim 3, wherein the step of incubating comprises incubating on ice.

5. The method of claim 3, wherein the step of incubating comprises incubating at room temperature.

6. The method of claim 2, wherein the method further comprises, after step b), a step of coating the shrimp pellet feed with fish oil.

* * * * *

SEQUENCE LISTING

```
<160> NUMBER OF SEQ ID NOS: 3

<210> SEQ ID NO 1
<211> LENGTH: 615
<212> TYPE: DNA
<213> ORGANISM: Penaeus vannamei

<400> SEQUENCE: 1

atggatcttt ctttcactct ttcggtcgtg tcggccatcc tcgccatcac tgctgtgatt     60

gctgtattta ttgtgatttt taggtatcac aacactgtga ccaagaccat cgaaacccac    120

acagacaata tcgagacaaa catggatgaa aacctccgca ttcctgtgac tgctgaggtt    180

ggatcaggct acttcaagat gactgatgtg tcctttgaca gcgacacctt gggcaaaatc    240

aagatccgca atggaaagtc tgatgcacag atgaaggaag aagatgcgga tcttgtcatc    300

actcccgtgg agggccgagc actcgaagtg actgtggggc agaatctcac ctttgaggga    360

acattcaagg tgtggaacaa cacatcaaga aagatcaaca tcactggtat gcagatggtg    420

ccaaagatta acccatcaaa ggcctttgtc ggtagctcca acacctcctc cttcaccccc    480

gtctctattg atgaggatga agttggcacc tttgtgtgtg gtaccacctt tggcgcacca    540

attgcagcta ccgccggtgg aaatcttttc gacatgtacg tgcacgtcac ctactctggc    600

actgagaccg agtaa                                                     615
```

-continued

<210> SEQ ID NO 2
<211> LENGTH: 615
<212> TYPE: DNA
<213> ORGANISM: Penaeus vannamei

<400> SEQUENCE: 2
atggatcttt ctttcactct ttcggtcgtg tcggccatcc tcgccatcac tgctgtgatt 60
gctgtattta ttgtgatttt taggtatcac aacactgtga ccaagaccat cgaaacccac 120
acagacaata tcgagacaaa catggatgaa aacctccgca ttcctgtgac tgctgaggtt 180
ggatcaggct acttcaagat gactgatgtg tcctttgaca gcgacacctt gggcaaaatc 240
aagatccgca atggaaagtc tgatgcacag atgaaggaag aagatgcgga tcttgtcatc 300
actcccgtgg agggccgagc actcgaagtg actgtggggc agaatctcac ctttgaggga 360
acattcaagg tgtggaacaa cacatcaaga aagatcaaca tcactggtat gcagatggtg 420
ccaaagatta acccatcaaa ggcctttgtc ggtagctcca acacctcctc cttcaccccc 480
gtctctattg atgaggatga agttggcacc tttgtgtgtg gtaccacctt tggcgcacca 540
attgcagcta ccgccggtgg aaatcttttc gacatgtacg tgcacgtcac ctactctggc 600
actgagaccg agtaa 615

<210> SEQ ID NO 3
<211> LENGTH: 1302
<212> TYPE: DNA
<213> ORGANISM: Penaeus vannamei

<400> SEQUENCE: 3
gctagcgttt tagcagctgg tgatctttct ttcactcttt cggtcgtgtc ggccatcctc 60
gccatcactg ctgtgattgc tgtatttatt gtgattttta ggtatcacaa cactgtgacc 120
aagaccatcg aaacccacac agacaatatc gagacaaaca tggatgaaaa cctccgcatt 180
cctgtgactg ctgaggttgg atcaggctac ttcaagatga ctgatgtgtc ctttgacagc 240
gacaccttgg gcaaaatcaa gatccgcaat ggaaagtctg atgcacagat gaaggaagaa 300
gatgcggatc ttgtcatcac tcccgtggag ggccgagcac tcgaagtgac tgtggggcag 360
aatctcacct ttgagggaac attcaaggtg tggaacaaca catcaagaaa gatcaacatc 420
actggtatgc agatggtgcc aaagattaac ccatcaaagg cctttgtcgg tagctccaac 480
acctcctcct tcacccccgt ctctattgat gaggatgaag ttggcacctt tgtgtgtggt 540
accacctttg gcgcaccaat tgcagctacc gccggtggaa atcttttcga catgtacgtg 600
cacgtcacct actctggcac tgagaccgag ggtggtggtg gttctggtgg tggtggttct 660
ggtggtggtg gttctcacat gtgggggggtt tacgccgcta tactggcggg tttgacattg 720
atactcgtgg ttatatctat agttgtaacc aacatagaac ttaacaagaa attggacaag 780
aaggataaag acgcctaccc tgttgaatct gaaataataa acttgaccat taacggtgtt 840
gctagaggaa accactttaa ctttgtaaac ggcacattac aaaccaggaa ctatggaaag 900
gtatatgtag ctggccaagg aacgtccgat tctgaactgg taaaaaagaa aggagacata 960
atcctcacat ctttacttgg agacggagac cacacactaa atgtaaacaa agccgaatct 1020
aaagaattag aattgtatgc aagagtatac aataatacaa agagggatat aacagtggac 1080
tctgtttcac tgtctccagg tctaaatgct acaggaaggg aattttcagc taacaaattt 1140
gtattatatt tcaaaccaac agttttgaag aaaaatagga tcaacacact tgtgtttgga 1200

-continued

| | | |
|---|---|---|
| gcaacgtttg acgaagacat cgatgataca aataggcatt atctgttaag tatgcgattt | 1260 |
| tctcctggca atgatctgtt taaggttggg gaaaaagaat tc | 1302 |